US005976537A

United States Patent [19]
Mengeling et al.

[11] Patent Number: 5,976,537
[45] Date of Patent: Nov. 2, 1999

[54] PORCINE REPRODUCTIVE AND RESPIRATORY SYNDROME VACCINE

[75] Inventors: William L. Mengeling, Ames; Kelly M. Lager, Nevada; Ann C. Vorwald, Ames, all of Iowa

[73] Assignee: The United States of America as represented by the Secretary of Agriculture, Washington, D.C.

[21] Appl. No.: 08/674,475

[22] Filed: Jul. 2, 1996

[51] Int. Cl.$^6$ .......................... A61K 39/00; A61K 39/12; C12N 7/08
[52] U.S. Cl. ...................... 424/184.1; 424/204.1; 424/211.1; 424/209.1; 424/218.1; 424/815; 435/235.1; 435/236; 435/237; 435/239
[58] Field of Search .................. 424/184.1, 204.1, 424/211.1, 209.1, 218.1, 815; 435/235.1, 236, 237, 239

[56] References Cited

U.S. PATENT DOCUMENTS 5,476,778   12/1995   Chladek et al. ...................... 435/235.1

FOREIGN PATENT DOCUMENTS 0587780   2/1995   European Pat. Off. ....... A61K 39/12

OTHER PUBLICATIONS

Done, S. H., et al., "Porcine Reproductive and Respiratory Syndrome (PRRS): A Review, with Emphasis on Pathological, Virological and Diagnostic Aspects", Br. Vet J., 1996, 152, pp. 153–174.

Gorcyca, D., et al., "RespPRRS: A New Tool for the Prevention and Control of PRRS in Pigs", American Association of Swine Practitioners, pp. 1–22, 1995.

Hesse, R. A., et al., "Efficacy of Prime Pac PRRS in Controlling PRRS Reproductive Disease: Heterologous Challenge", American Association of Swine Practitioners, pp. 107–110, 1996.

Lager, K. M., et al., "Limited Cross–Protection Between Two Strains of Porcine Reproductive and Respiratory Syndrome Virus in Pregnant Swine", Abstracts, Second International Symposium on Porcine Reproductive and Respiratory Syndrome (PRRS), Aug. 9–10, 1995, Copenhagen, Denmark, p. 10.

Mengeling, William L., et al., "Comparison among stains of porcine reproductive and respiratory syndrome virus for their ability to cause reproductive failure", AJVR, vol. 57, No. 6, Jun. 1996, pp. 834–839.

*Primary Examiner*—Frank C. Eisenschenk
*Assistant Examiner*—Ali R. Salimi
*Attorney, Agent, or Firm*—M. Howard Silverstein; Curtis P. Ribando; John D. Fado

[57] ABSTRACT

Vaccines against porcine reproductive and respiratory syndrome (PRRS) have been produced by attenuation of wild type strains of the virus selected from the group of attenuated NADC-8, attenuated NADC-9 and attenuated NVSL-14. These vaccines are useful in monovalent, bivalent or polyvalent vaccines.

14 Claims, No Drawings

PORCINE REPRODUCTIVE AND RESPIRATORY SYNDROME VACCINE

BACKGROUND OF THE INVENTION

1. Field of the Invention

This invention relates to a vaccine for porcine reproductive and respiratory syndrome (PRRS) comprising one or more strains of attenuated porcine reproductive and respiratory syndrome virus (PRRSV).

A previously unknown disease of pigs, PRRS was recognized for the first time in the United States in North Carolina in 1987. From there, it quickly spread throughout all of the major swine producing areas of North America. It next appeared in Europe, and today PRRS has almost worldwide distribution. Many swine producers, government officials, and veterinarians believe that PRRS is currently one of the most serious economic threats faced by the swine industries worldwide.

As its name implies, PRRS is characterized clinically by its ability to cause reproductive failure (in pregnant females, especially when initially infected late in gestation), and respiratory tract illness (in pigs of all ages, but most common and severe in young pigs). Infection with PRRSV is also thought to be immunosuppressive and thus potentiate the effects of other swine pathogens. On the basis of retrospective serological studies, it also has become evident that many infections of swine with PRRSV are either subclinical or result in less obvious clinical signs. Therefore, the PRRSV often gains access to a herd and spreads extensively before its presence is first detected.

The virus can persist in an infected host for at least several months. Such "carriers" perpetuate the infection and make control of the disease extremely difficult. As a consequence, the most effective means for reducing the economic impact of PRRS is to vaccinate (immunize) potentially susceptible pigs before they are exposed to virulent field virus.

2. Description of the Prior Art

Only a single attenuated vaccine, (manufactured by Boehinger Ingelheim and distributed by NOBL Laboratories) prepared from a single strain of PRRSV, is commercially available. It is only licensed for use in pigs between 3 and 18 weeks of age for the prevention of respiratory tract illness (Gorcyca et al., 1995).

Another attenuated vaccine has been described for the prevention of reproductive failure (Hesse et al., 1996). It is prepared from a single strain of PRRSV and has only been tested against a single strain of PRRSV. The challenge strain is described as heterologous on the basis of the anamnestic response of vaccinated gilts following challenge; however, no other evidence has been presented to establish that the two strains, i.e., the one used for the vaccine and the one used for challenge of immunity, are genetically or antigenically different.

There are two known major serotypes of PRRSV (Done et al., 1996, herein incorporated by reference). One (prototype Lelystad) is representative of at least most strains that have been isolated in Western Europe. The other (prototype ATCC 2332) is representative of at least most strains isolated in North America and Asia. The two prototypes are easily distinguished serologically in that antisera from pigs exposed to one prototype react poorly or not at all with the other. There also are antigenic variants within prototypes (Meng et al., 1995), and base sequence differences among strains isolated in North America have allowed for their differentiation (Wesley et al., 1996).

A study, wherein sows previously exposed to PRRSV strain NADC-8 were protected when subsequently exposed during gestation to either virulent strain Lelystad or virulent strain NADC-8 (Lager et al., 1995), provided evidence that at least one American isolate could protect against the reproductive failure caused by either an American or European isolate of PRRSV.

SUMMARY OF THE INVENTION

We have now discovered and developed attenuated vaccines for the prevention of PRRSV-induced reproductive failure or respiratory disease of swine. The vaccines are derived from three strains of PRRSV that were isolated in the United States from pigs affected with PRRS.

In accordance with this discovery, it is an object of this invention to provide vaccines for PRRS that are safe, even if administered during late gestation when PRRSV is most likely to cross the placenta and cause reproductive failure.

It is also an object of the invention to provide vaccines that are effective, even when the vaccinated female is exposed (challenged) during late gestation to a mixture of heterologous field strains of PRRSV.

Another object of the invention is to provide attenuated strains of PRRS that would be useful in a polyvalent vaccine against PRRS.

Other objects and advantages of this invention will become readily apparent from the ensuing description.

DEPOSIT OF BIOLOGICAL MATERIAL

Attenuated strains NADC-8, NADC-9 and NVSL-14 at the 81st passage level were deposited on Jul. 2, 1996 under the terms of the Budapest Treaty at the American Type Culture Collection in Rockville, Md., and have been assigned Accession Nos. ATCC VR-2355, ATCC VR-2536, and ATCC VR-2537, respectively.

DETAILED DESCRIPTION OF THE INVENTION

"Vaccine" is defined herein in its broad sense to refer to any type of biological agent in an administratable form capable of stimulating an immune response in an animal inoculated with the vaccine. For purposes of this invention, the vaccine may comprise as the viral agent either the virus itself or an immunogenic (antigenic) component of the virus.

The vaccine of the invention is prepared from any one or more of the three attenuated strains of PRRSV: NADC-8, NADC-9 and NVSL-14. Each strain has been individually tested for safety and efficacy, and it is contemplated that a polyvalent vaccine comprised of all of the strains would be at least as safe and effective as each monovalent vaccine and might provide even broader immunity to virulent field strains of PRRSV.

Three strains of PRRSV (strains NADC-8, NADC-9, and NVSL-14) were selected for development as vaccines.

Strain NADC-8 was isolated in Iowa in 1992 from the only live pig of a litter that otherwise was presumed to have died as a result of natural infection with PRRSV (Lager et al., 1996). Selection of this strain was based on our expectation that it would be an excellent representative of strains causing reproductive failure from the circumstances of its initial isolation and from subsequent experimental exposure of pregnant gilts (Mengeling et al., Am. J. Vet. Res., 1996).

Strain NADC-9 was isolated in Iowa in 1993 from the lung of a pig that displayed lesions of pulmonary consolidation, presumably as a result of natural infection with PRRSV (Mengeling et al., J. Vet. Diagn. Invest., 1996). Selection of this strain was based on our expectation that it would be an excellent representative of strains causing respiratory tract illness.

Strain NVSL-14 originated in Nebraska and was selected from a group of 20 field strains of PRRSV that were provided to us by the National Veterinary Services Laboratories. Selection of this strain was based on preliminary data that indicated that, compared to some other strains we tested, it replicated to high infectivity titer in a susceptible cell line (MARC-145).

Each of the strains was first purified by 3 terminal dilutions and then attenuated by a unique process of rapid serial passage (at daily intervals) in MARC-145 cells with dilution of inoculum ($\leq 1:50,000$) at each passage. Each was tested for attenuation (safety) after its 84th and after its 250th passage in cell culture by administration to susceptible pregnant gilts late in gestation—at a time when similar exposure to nonattenuated field strains of PRRSV would cause reproductive failure (Mengeling et al., Am. J. Vet. Res., 1996). The purpose of the applied attenuation procedure was to select a mutant population of each of the strains under study that would replicate to a high enough titer in cell culture to allow commercial vaccine production, would be safe even if administered to pregnant females during late gestation (the time of greatest susceptibility), and would induce the formation of antibody and protective immunity in vaccinated swine.

Although attenuation is recognized as an established procedure for reducing the virulence of a virus, the ability to attenuate a virus to the point that it can be safely administered to animals without inducing the disease, while maintaining its immunogenicity, remains highly unpredictable. Contemplated for use within the scope of this invention are attenuated viruses derived from the aforementioned strains which have lesser virulence (i.e., reduced ability to cause clinical disease) at a statistically significant level ($P \geq 0.5$) than the corresponding wild type strain, and which also imparts to susceptible swine active immunity to challenge from either the same or different strains of PRRSV at a level that is significantly greater than the innate resistance of a non-vaccinated control. In the most preferred embodiment of the invention, the immunity imparted by the attenuated vaccine virus is not significantly less than that imparted by the corresponding wild type strain. The aforementioned immunities are typically measured in terms of a population of animals. From the data given below in the examples, it would appear that at least about 84 serial passages, and more preferably, at least about 150 serial passages, are necessary to achieve the desired level of attenuation. In the most preferred embodiment of the invention, the virus is serially passaged in cell culture at least about 250 times.

Though the subject vaccines were evaluated principally on the basis of their safety and efficacy regarding the effects of PRRS on porcine reproductively, it is understood that the vaccines would also be useful in protecting against the respiratory manifestations of the disease.

The vaccine virus is prepared for administration by formulation in an effective immunization dosage with a pharmaceutically acceptable carrier or diluent, such as physiological saline or tissue culture medium. The expression "effective immunization dosage" is defined as being that amount which will induce immunity in a pig against challenge by a virulent strain of PRRSV at levels as previously described. Determination of actual dosage amounts would be fully within the skill of a person in the art. Based on the examples given below, it is contemplated that a single dosage of approximately $10^4$–$10^6$ median cell culture infectious units ($CCID_{50}$) would be effective. The vaccines can be administered oronasally or by injection. The vaccine is advisedly administered to gilts at least two months prior to mating as an extra precaution against vaccine-induced reproductive failure. Ideally, all pigs are vaccinated within the first few weeks after birth in order to protect against the respiratory symptoms of the disease.

Appropriate adjuvants as known in the art may be included in the vaccine formulation. As previously mentioned, the subject vaccines may be used individually, or they may be combined together in any combination in the formulation of a polyvalent vaccine.

The following examples are used to illustrate successful attainment of the objectives of the invention. None are intended to limit its scope of applicability.

EXAMPLE 1

Objective

To test the ability of the selected strains (NADC-8, NADC-9, and NVSL-14) of PRRSV before attenuation to cause reproductive failure in pregnant gilts.

When gilts (principals) were at or about 90 days of gestation they were each exposed oronasally to 10 ml of inoculum that contained $10^7$ median cell culture infectious units ($CCID_{50}$) of PRRSV. Day 90 of gestation was selected on the basis of a previous study that indicated this was the time of greatest susceptibility (Mengeling et al., 1994). All gilts, including controls (i.e., pregnant gilts not exposed to PRRSV) were from the same source herd and were treated similarly except for PRRSV exposure. Results are summarized in Table 1, below. The virulence of these strains before attenuation was evident by the fact that the percentage of liveborn pigs of principal gilts was only about 55% (55%, 52%, and 63% of the pigs of gilts exposed to strains NADC-8, NADC-9, and NVSL-14, respectively) compared to 95% of those of control gilts.

EXAMPLE 2

Objective

To test the ability of selected strains (NADC-8, NADC-9, and NVSL-14) of PRRSV after attenuation by 84 passages in cell culture to cause reproductive failure in pregnant gilts.

Exposure to PRRSV (i.e., dose, route, and stage of gestation) was the same as that of Example 1. Results are summarized in Table 2, below. Attenuation of all 3 strains by cell culture passage was evident by the fact that the percentage of liveborn pigs was similar for principal gilts (95%, 95%, and 92% of the pigs of gilts exposed to strains NADC-8, NADC-9, and NVSL-14, respectively) and control gilts (95%).

EXAMPLE 3

Objective

To test the ability of selected strains (NADC-8, NADC-9, and NVSL-14) of PRRSV after attenuation by 250 passages in cell culture to cause reproductive failure in pregnant gilts.

Exposure to PRRSV (i.e., dose, route, and stage of gestation) was the same as that of Examples 1 and 2. Results are summarized in Table 3, below. Attenuation of all 3 strains by cell culture passage was evident by the fact that the percentage of liveborn pigs was similar for principal gilts (100%, 100%, and 95% of the pigs of gilts exposed to strains NADC-8, NADC-9, and NVSL-14, respectively) and control gilts (100%).

EXAMPLE 4

Objective

To test the ability of selected strains (NADC-8, NADC-9, and NVSL-14) of PRRSV at different levels of attenuation to cross the placenta and affect postnatal survival of liveborn pigs.

Represented here are the liveborn pigs of gilts included in Tables 1, 2, and 3. Not represented here are the stillborn pigs and dead fetuses of these same gilts. It was assumed that most of the dead pigs and fetuses of principal gilts, especially those of principal gilts exposed to PRRSV that had not been attenuated by cell culture passage (Table 1), had been infected in utero and had died as a result. However, it was not always possible to isolate PRRSV (data not shown) because of its instability in dead tissues. Results relative to postnatal survival, incidence of congenital infection, and postnatal transmission of virus from congenitally infected pigs to litter mates are summarized in Table 4, below. An increase in postnatal survival, namely 55% to 75%, 64% to 88%, and 59% to 85% for pigs of gilts exposed to strains NADC-8, NADC-9, and NVSL-14, respectively, before and after 250 cell culture passages, is further evidence of attenuation. In addition, the incidence of congenital infection and subsequent transmission of PRRSV from congenitally infected pigs to litter mates is much less in pigs of gilts exposed to the strains passed 250 times in cell culture than in pigs of gilts exposed to the same strains passed fewer times (i.e., 1, 3, or 84 times) in cell culture.

EXAMPLE 5

Objective

To determine the pre- and postnatal (up to days 14–21 depending on when pigs were euthanized at the termination of the experiment) survival of pigs of gilts exposed to different passage levels of strains NADC-8, NADC-9, and NVSL-14 of PRRSV.

Table 5, below, summarizes data from gilts and pigs included in Tables 1–4. Attenuation of the 3 strains by cell culture passage was evident by the fact that the survival rate of pigs of principal gilts exposed to the 250 cell culture passage (considering death in utero and postnatal death) was similar to that of pigs of control gilts, namely, 86% for NADC-8, 88% for NADC-9, 81% for NVSL-14, and 87% for controls. These values are in contrast to those for pigs of gilts exposed to the same strains with 3 or fewer passages in cell culture, namely, 22% for NADC-8, 33% for NADC-9, and 37% for NVSL-14.

EXAMPLE 6

Objective

To determine if gilts and their pigs would have a humoral antibody response to PRRSV following exposure to each of the strains of PRRSV at each cell culture passage level.

Sera were collected from gilts just before they were exposed to PRRSV and several times during the ensuing 30 days following exposure. Sera were tested by indirect immunofluorescence microscopy for antibody against strain NADC-8 (which previously had been shown to be cross reactive with each of the other strains of the study). Results are summarized as follows. All gilts except one gilt exposed to the 250th cell culture passage of strain NADC-9 had a serum antibody response to PRRSV by at least day 14 postexposure. Some pigs had serum antibody for PRRSV at birth as a result of congenital infection. All pigs that suckled seropositive gilts had serum antibody for PRRSV after ingestion of colostrum.

EXAMPLE 7

Objective

To determine if pregnant sows previously exposed as pregnant gilts to attentuated strains NADC-8, NADC-9, and NVSL-14 would be immune to subsequent exposure to virulent PRRSV.

The study was performed with pregnant sows previously exposed to the 84th cell culture passage of each of the strains (hereafter referred to as vaccinated sows) and their controls (Table 2). For challenge, each vaccinated sow at or about day 90 of gestation was exposed oronasally to 10 ml of inoculum containing $10^6$ $CCID_{50}$ of each of 20 virulent field strains of PRRSV (including strains NADC-8, NADC-9, and NVSL-14). These strains all differed genetically to some degree as previously shown by sequencing of open reading frame 5 that codes for the major envelope glycoprotein of the virion (Wesley et al., 1996). They had been isolated from widely different geographical areas including Canada, Guatemala, and various states of the United States. The purpose of this selection of numerous strains was to provide the most rigorous challenge of immunity in that there has been some indication that strains may be poorly cross protective. Results are summarized in Table 6, below. The protective immunity provided by each of the strains is indicated by the fact that the reproductive performance of all vaccinated sows far exceeded that of the corresponding control, i.e., 100%, 100% and 96% vs 23%. Moreover, only 1 of 73 liveborn pigs of vaccinated sows was found to be infected at birth, whereas, 5 of the 6 liveborn pigs of control sows were found to be infected at birth.

TABLE 1

| Group | Strain[1] | No. gilts (litters) | No. pigs born Alive | Dead[2] | % born alive |
|---|---|---|---|---|---|
| I | NADC-8 | 10 | 61 | 50 | 55 |
| II | NADC-9 | 2 | 14 | 13 | 52 |
| III | NVSL-14 | 2 | 17 | 10 | 63 |
| IV | Control[3] | 13 | 143 | 8 | 95 |

[1]After 3 or fewer serial passages in cell culture.
[2]Excluding mummified fetuses that died before gilts were exposed to PRRSV.
[3]Pregnant gilts from the same herd and treated similarly except for exposure to PRRSV. Controls of Tables 2 and 3 are included in this total.

TABLE 2

| Group | Strain[1] | No. gilts (litters) | No. pigs born Alive | Dead[2] | % born alive |
|---|---|---|---|---|---|
| I | NADC-8 | 2 | 19 | 1 | 95 |
| II | NADC-9 | 2 | 20 | 1 | 95 |
| III | NVSL-14 | 2 | 23 | 2 | 92 |
| IV | Control[3] | 2 | 19 | 1 | 95 |

[1] After 84 serial passages in cell culture.
[2]Excludes mummified fetuses that died before gilts were exposed to PRRSV.
[3]Pregnant gilts from the same herd and treated similarly except for exposure to PRRSV.

TABLE 3

| Group | Strain[1] | No. gilts (litters) | No. pigs born[2] Alive | Dead | % born alive |
|---|---|---|---|---|---|
| I | NADC-8 | 2 | 29 | 0 | 100 |
| II | NADC-9 | 2 | 16 | 0 | 100 |

TABLE 3-continued

| | | No. gilts | No. pigs born[2] | | % born |
|---|---|---|---|---|---|
| Group | Strain[1] | (litters) | Alive | Dead | alive |
| III | NVSL-14 | 2 | 20 | 1 | 95 |
| IV | Control[3] | 4 | 42 | 0 | 100 |

[1]After 250 serial passages in cell culture.
[2]Excludes mummified fetuses that died before gilts were exposed to PRRSV.
[3]Pregnant gilts from the same herd and treated similarly except for exposure to PRRSV.

TABLE 4

| Group | Table[1] | Strain | Cell culture passage | No. gilts (litter) | No. pigs alive (infected) Day 0 | No. pigs alive (infected) Day 14–21[2] | % of live pigs infected Day 0 | % of live pigs infected Day 14–21 | % Survival between days 0 and 14–21 |
|---|---|---|---|---|---|---|---|---|---|
| I | 1 | NADC-8 | 1 | 10 | 61(34) | 35(26) | 56 | 74 | 55 |
|   | 2 | " | 84 | 2 | 19(10) | 16(16) | 53 | 100 | 84 |
|   | 3 | " | 250 | 2 | 16(3) | 12(2) | 19 | 17 | 75 |
| II | 1 | NADC-9 | 1 | 2 | 14(8) | 9(9) | 57 | 100 | 64 |
|   | 2 | " | 84 | 2 | 20(4) | 15(15) | 20 | 100 | 75 |
|   | 3 | " | 250 | 2 | 16(0) | 14(1) | 0 | 7 | 88 |
| III | 1 | NVSL-14 | 3 | 2 | 17(11) | 10(10) | 65 | 100 | 59 |
|   | 2 | " | 84 | 2 | 23(8) | 16(16) | 35 | 100 | 70 |
|   | 3 | " | 250 | 2 | 20(0) | 17(1) | 0 | 6 | 85 |
| IV | 1–2 | Control | ... | 13 | 143(0) | 132(0) | 0 | 0 | 92 |

[1]Tables 1, 2, and 3 document the reproductive performance of the gilts included here, i.e. the number of live and dead pigs at day 0.
[2]Many liveborn pigs died, or were euthanized when near death, before the remainder of the litter was euthanized at days 14, 15, or 21.

TABLE 5

| Group | Table[1] | Strain | Cell culture passage | No. gilts (litter) | No. fetuses (pigs) Alive at[1] exposure | No. fetuses (pigs) Died[2] in utero | No. fetuses (pigs) Died[3] postnatally | Survival No. | Survival % |
|---|---|---|---|---|---|---|---|---|---|
| I | 1 | NADC-8 | 1 | 10 | 111 | 61 | 26 | 24 | 22 |
|   | 2 | " | 84 | 2 | 20 | 1 | 3 | 15 | 75 |
|   | 3 | " | 250 | 2 | 29 | 0 | 4 | 25 | 86 |
| II | 1 | NADC-9 | 1 | 2 | 27 | 13 | 5 | 9 | 33 |
|   | 2 | " | 84 | 2 | 21 | 1 | 5 | 15 | 71 |
|   | 3 | " | 250 | 2 | 16 | 0 | 2 | 14 | 88 |
| III | 1 | NVSL-14 | 3 | 2 | 27 | 10 | 7 | 10 | 37 |
|   | 2 | " | 84 | 2 | 25 | 2 | 7 | 16 | 64 |
|   | 3 | " | 250 | 2 | 21 | 1 | 3 | 17 | 81 |
| IV | 1–2 | Control | ... | 13 | 151 | 8 | 11 | 132 | 87 |

[1]The number of fetuses alive at the time gilts were exposed to PRRSV.
[2]Includes stillborn pigs.
[3]Before euthanasia of litters when 14, 15, or 21 days of age.

TABLE 6

| | Vaccine | No. gilts | No. pigs born | | % born |
|---|---|---|---|---|---|
| Group | strain | (litters) | Alive | Dead | alive |
| I | NADC-8 | 1 | 12 | 0 | 100 |
| II | NADC-9 | 2 | 23 | 0 | 100 |
| III | NVSL-14 | 2 | 23 | 1 | 96 |
| IV | Control | 2 | 6 | 20 | 23 |

REFERENCES

Done S H, Paton D J, White M E C. Porcine reproductive and respiratory syndrome (PRRS): A review, with emphasis on pathological, virological and diagnostic aspects. Br Vet J 1996;152:153–174.

Gorcyca D, Chladek D, Behan W, Polson D, Roof M, Doitchenoff D. RespPRRS: A new tool for the prevention and control of PRRS in pigs, in proceedings. Am Assoc Swine Pract 1995:1–22.

Hesse R A, Couture L P, Lau M L, Wunder K K, Wasmoen T L. Efficacy of Prime Pac PRRS in controlling PRRS reproductive disease: Heterologous challenge, in proceedings. Am Assoc Swine Pract 1996:107–110.

Lager K M, Mengeling W L, Brockmeier S L. Limited cross-protection between two strains of porcine reproductive and respiratory syndrome virus in pregnant swine, in proceedings. 2nd Int Symp on Porcine Reproductive and Respiratory Syndrome, Copenhagen, Denmark (1995).

Lager K M, Mengeling W L, Brockmeier S L. Effect of porcine reproductive and respiratory syndrome virus on conception in gilts following post-coital, intrauterine inoculation. Vet Rec 1996;138:227–228.

Meng X J, Paul P S, Halbur P G, Lum M A. Phylogenetic analyses of putative M (ORF 6) and N (ORF 7) genes of porcine reproductive and respiratory syndrome virus (PRRSV): Implication for the existence of two genotypes of PRRSV in the U.S.A. and Europe. Arch Virol 1995;140:745–755.

Mengeling W L, Lager K M, Vorwald A C. Temporal characterizations of transplacental infection of porcine fetuses with porcine reproductive and respiratory syndrome virus. Am J Vet Res 1994;55:1391–1398.

Mengeling W L, Lager K M, Vorwald A C. Diagnosis of porcine reproductive and respiratory syndrome. J Vet Diagn Invest 1995;7:3–16.

Mengeling W L, Lager K M, Vorwald A C. Alveolar macrophages as a diagnostic sample for detecting natural infection of pigs with porcine reproductive and respiratory syndrome virus. J Vet Diagn Invest 1996;8:238–240.

Mengeling W L, Vorwald A C, Lager K M, Brockmeier S L. Comparison among strains of porcine reproductive and respiratory syndrome virus as to their ability to cause reproductive failure. Am J Vet Res 1996;57:834–840.

Wesley R D, Mengeling W L, Lager K M. Differentiation of vaccine (Strain RespPRRS®) and field strains of porcine reproductive and respiratory syndrome virus by restriction enzyme analysis, in proceedings. Am Assoc Swine Pract 1996:141–143.

We claim:

1. A vaccine useful against porcine reproductive and respiratory syndrome comprising: (1) in an effective immunization dosage, an attenuated virus selected from the group consisting of attenuated ATCC VR-2535, attenuated ATCC VR-2536 and attenuated ATCC VR-2537, wherein said attenuated virus is characterized by significantly lower infectivity after at least 84 serial passages than the corresponding wild type strain; and (2) a pharmaceutically acceptable carrier or diluent.

2. The vaccine of claim 1 wherein said virus is attenuated ATCC VR-2535.

3. The vaccine of claim 1 wherein said virus is attenuated ATCC VR-2536.

4. The vaccine of claim 1 wherein said virus is attenuated ATCC VR-2537.

5. The vaccine of claim 1 wherein said vaccine is polyvalent and comprises two or more attenuated viruses selected from the group consisting of attenuated ATCC VR-2535, attenuated ATCC VR-2536 and attenuated ATCC VR-2537.

6. The vaccine of claim 1 wherein said attenuated virus is the product of the wild type virus having been serially passaged at least 250 times.

7. The vaccine of claim 1 and further comprising an adjuvant.

8. A method for protecting a swine against porcine reproductive and respiratory syndrome comprising inoculating said swine with an effective immunization dosage of an attenuated virus selected from the group consisting of attenuated ATCC VR-2535, attenuated ATCC VR-2536 and attenuated ATCC VR-2537 wherein said attenuated virus is formulated in a pharmaceutically acceptable carrier or diluent and is characterized by significantly lower infectivity after at least 84 serial passages than the corresponding wild type strain.

9. The method of claim 8 wherein said virus is attenuated ATCC VR-2535.

10. The method of claim 9 wherein said virus is attenuated ATCC VR-2536.

11. The method of claim 9 wherein said virus is attenuated ATCC VR-2537.

12. The method of claim 9 wherein said vaccine is polyvalent and comprises two or more attenuated viruses selected from the group consisting of attenuated ATCC VR-2535, attenuated ATCC VR-2536 and attenuated ATCC VR-2537.

13. The method of claim 8 wherein said attenuated virus is the product of the wild type virus having been serially passaged at least 250 times.

14. The method of claim 8 wherein said vaccine further comprises an adjuvant.

* * * * *